United States Patent [19]
Cady et al.

[11] Patent Number: 5,266,333
[45] Date of Patent: Nov. 30, 1993

[54] WATER DISPERSIBLE AND WATER SOLUBLE CARBOHYDRATE POLYMER COMPOSITIONS FOR PARENTERAL ADMINISTRATION OF GROWTH HORMONE

[75] Inventors: Susan M. Cady, Yardley, Pa.; Richard Fishbein, Skillman, N.J.; Ulf Schröder; Hakan Eriksson, both of Lund, Sweden; Brenda L. Probasco, New Egypt, N.J.

[73] Assignee: American Cyanamid Company, Wayne, N.J.

[21] Appl. No.: 400,838

[22] Filed: Aug. 30, 1989

Related U.S. Application Data

[63] Continuation of Ser. No. 830,158, Feb. 20, 1986, abandoned, which is a continuation-in-part of Ser. No. 717,417, Mar. 29, 1985, abandoned.

[30] Foreign Application Priority Data

Mar. 6, 1985 [SE] Sweden ............................... 8501094

[51] Int. Cl.$^5$ ..................... A61K 9/08; A61K 9/10; A61K 47/36
[52] U.S. Cl. .................... 424/488; 424/422; 530/813; 530/814
[58] Field of Search ............... 424/473, 484, 486, 488; 530/399, 813, 814

[56] References Cited

U.S. PATENT DOCUMENTS

| | | |
|---|---|---|
| 3,904,631 | 9/1975 | Elslager et al. ............ 435/118 |
| 4,003,792 | 1/1977 | Mill et al. . |
| 4,124,705 | 11/1978 | Rothman et al. . |
| 4,357,423 | 11/1982 | Cox et al. . |
| 4,452,775 | 6/1984 | Kent . |
| 4,521,409 | 6/1985 | Bauman . |
| 4,585,754 | 4/1986 | Meisner et al. . |
| 4,604,377 | 8/1986 | Fernandes et al. ............ 514/2 |
| 4,713,249 | 12/1987 | Schroder . |
| 4,769,027 | 9/1988 | Baker et al. ............ 424/473 |
| 4,824,938 | 4/1989 | Koyama et al. ............ 530/399 |

FOREIGN PATENT DOCUMENTS

| | | |
|---|---|---|
| 085036 | 8/1983 | European Pat. Off. . |
| 94157 | 11/1983 | European Pat. Off. . |
| 94157 | 11/1983 | European Pat. Off. . |
| 123291 | 10/1984 | European Pat. Off. . |
| 8400294 | 2/1984 | PCT Int'l Appl. . |
| 1345573 | 1/1974 | United Kingdom . |
| 1345573 | 1/1974 | United Kingdom . |
| 2160528 | 12/1987 | United Kingdom . |

Primary Examiner—Thurman K. Page
Assistant Examiner—E. J. Webman
Attorney, Agent, or Firm—Michael P. Morris

[57] ABSTRACT

The present invention relates to compositions of water dispersible and water soluble carbohydrate polymers and biologically active macromolecules of growth hormones, somatomedins, growth factors, and other biologically active fragments which are suitable for parenteral administration. The present invention also relates to a method for increasing and for maintaining increased levels of growth hormone in the blood of treated animals for extended periods of time, increasing weight gains in animals, and increasing milk production of lactating animals by the administration of the compositions of the invention.

12 Claims, No Drawings

WATER DISPERSIBLE AND WATER SOLUBLE CARBOHYDRATE POLYMER COMPOSITIONS FOR PARENTERAL ADMINISTRATION OF GROWTH HORMONE

This application is a continuation of co-pending application Ser. No. 06/830,158, filed on Feb. 20, 1986, now abandoned, which is a continuation-in-part of prior application Ser. No. 06/717,417, filed on Mar. 29, 1985, abandoned.

BACKGROUND OF THE INVENTION

The desirability of providing dosage forms of biologically active substances which release the substance in a controlled manner and thus reduce the frequency of administration is well established.

Recent developments in the area of controlling the release of drugs include those disclosed in European Patent Application 81305426.9 and European Patent Application 82300416.3 which describe methods for controlling the release of drugs by microencapsulation and containment within a biodegradable matrix, respectively. U. Schroder J. Immunological Methods 70,127-132 (1984) and Biomaterials 5(2) 100-104 (1984) describes the fabrication and use of carbohydrate spheres as a crystalline slow release matrix for biologically active substances, where controlled release is obtained by erosion of the matrix. S. L. Davies et al, in The Journal of Dairy Science Vol. 66 No. 9, pp 1980-1981 (1983) describes a beeswax implant for administering growth hormone (oGH), while U.S. Pat. No. 4,452,775 describes a cholesterol matrix delivery system for sustained release of macromolecules including a variety of growth hormones.

The above references disclose a variety of solid matrix systems for the administration of biologically active substances. It is an object of the present invention to provide aqueous compositions of water dispersible and soluble polymers, and growth hormones, which are water soluble and are suitable for parenteral administration in aqueous medium. It is another object of this invention to provide a method for increasing and maintaining increased levels of growth hormones in the blood of treated animals and humans for extended periods of time and obtaining beneficial effects such as increasing weight gains and increasing milk production in lactating animals, by parenteral administration of the aqueous compositions of the invention.

SUMMARY OF THE INVENTION

The invention includes biologically active compositions including water solutions of a biologically active macromolecule and a carbohydrate.

We have found that the compositions of the invention provide sustained release of growth hormones when administered parenterally as solutions, dispersions and pastes.

The invention relates to compositions for parenteral administration comprising a water soluble or water dispersible carbohydrate polymer, or a mixture of carbohydrate polymers, and a biologically active macromolecule, and water, or a buffered solution, or a pharmaceutically and pharmacologically acceptable solvent. The invention includes a method for administering and maintaining blood levels of biologically active macromolecules comprising parenterally administering compositions of the invention. The invention also includes a method for increasing milk production in dairy cows comprising parenterally administering compositions of the invention to the cows.

Biologically active macromolecules of the invention include e.g., growth hormones, somatomedins, growth factors, and other biologically active fragments. These macromolecules include growth hormones for example bovine, ovine, equine, porcine, and human growth hormones. However, other biologically active macromolecules may also be used within the scope of the invention, such as insulin.

Carbohydrates, such as dextran and starch, have until now been assumed to be inert regarding their capability to adsorb high molecular weight substances such as proteins. As an example of this it may be mentioned that dextran is used for the preparation of covalently cross-linked spheres (Sephadex, Pharmacia AB). These spheres are used for purification and for chemical characterization of proteins where very high demands on low unspecific adsorbtions of the proteins to the matrix are needed.

However, as described in this invention, when some carbohydrates are in solution, strong and not previously described interactions between carbohydrates and proteins are obtained. These interactions are very strong, and strong dissociating substances in high concentrations are needed to break the interaction between the carbohydrate and the protein.

Polymers preferred for use in the invention include carbohydrate polymers such as the dextrans, dextrins, alginates, starches and fractionated starches, glycogen, pullullan, agarose, cellulose, chitosan, carrageenan, and synthetic biopolymers, as well as gums such as xanthan gum, guar gum, locust bean gum, gum arabic, tragacanth gum, and karaya gum, derivatives thereof and mixtures thereof. These carbohydrate polymers, many of which are classified as polysaccharides or oligosaccharides or derivatives thereof, have the desirable properties of being inert to biological systems; they are well characterized and nontoxic; they are excretable from the body by normal routes; and, due to their water solubility and dispersion characteristics, they may readily be administered in aqueous compositions. The term water solubility for these polymers is meant to include the range of colloidal solution and dispersions.

Solvents suitable for use in the compositions of this invention include phosphate buffered saline (PBS) which contains $NaH_2PO_4 \cdot H_2O$ (0.025 Mol), $Na_2HPO_4$ (0.025 mol), and NaCl (0.15 mol) which has been adjusted to pH 7.1 and Carbonate Buffer Saline (CBS) which contains $Na_2CO_3$ (0.025 mol), $NaHCO_3$ (0.025 mol), and NaCl (0.15 mol) which has been adjusted to pH 9.4; and saline; alone in combination with other pharmaceutically and pharmocologically acceptable water miscible solvents.

Pharmaceutically and pharmacologically acceptable solvents frequently employed in biological preparations for parenteral administrations include a variety of liquid alcohols, glycols, esters, and amides. As such, these solvents find utility in the compositions of this invention.

The invention includes a way of preparing such compositions, including the complex formation of a protein to carbohydrate in a water solution, together with hydrophobic or a hydrophilic substance that may interfere with hydrophobic or hydrophilic interactions in the complex.

Additionally complex formation may be effected by methods already well-known in the literature which describes the derivatization of carbohydrates with various hydrophobic or charged moieties. Examples of hydrophobic derivatives can be mentioned such as cholesterol or Cibachrome blue, or charged groups such as sulfate or amino groups.

Hence, it is possible to influence complex formation by the use of various hydrophobic and/or hydrophilic substances that influence the hydrophobic or hydrophilic interactions in the complex during the formation of the complex.

Additionally, stabilizers and preservatives such as acids, esters, organic ammonium halides, sulfides, alcohols, amines, anilides or organomercury compounds at concentrations of up to 0.2% on a weight to volume basis may be added to the compositions of the invention to improve their stability. Preferred stabilizers for compositions of the invention include dehydroacetic acid and salts thereof, the sodium salt being most preferred; salicylanilide; sorbic acid and salts thereof, the potassium salt being most preferred; sodium nitrite and sodium nitrate.

By the use of detergents which break hydrophobic interactions, it has now been shown that it is this type of interaction which is dominating for some carbohydrates. A complex has, according to this invention, a size below 50 nanometer, but despite this, a complex bound protein can not be detected with the help of antibodies through an ELISA determination. That polyclonal antibodies are not able to be bound to the protein suggests that the protein is hidden by a carbohydrate.

It has now, surprisingly, been shown, that despite above-mentioned hiding, the protein still has its biological activity, since after injection in an animal, continuous and uniform dissociation of the complex over ten days is obtained. The dissociation in vivo is obtained with the help of the detergent systems within the body, i.e. systems that influence the hydrophobic or hydrophilic interactions in the complex. Alternatively one may, when preparing a complex, add such a substance like a detergent to ease the dissociation of the complex.

Preferred compositions of the invention are comprised of soluble carbohydrate polymer to biologically active macromolecule ratios on a weight basis of from 0.25/1.0 to 100.0/1.0. Soluble carbohydrate polymer to solvent ratio will of course vary depending upon the solubility of the carbohydrate and solvent employed. These preferred compositions having soluble carbohydrate polymer to biologically active macromolecule ratios of from 1.0/1.0 to 100/1 may be administered as aqueous pastes or solutions in water or buffered saline solutions. Higher ratios of water soluble polymer may of course also be employed. The quantity of water or buffered saline solution may vary depending upon the carbohydrate polymer and its solubility characteristics, as may the pH of the huffered saline solution. Aqueous compositions of the invention administered in vivo in a pH range of from about pH 3.0 to pH 10.0 having water to carbohydrate polymer ratios of 0.83 to 1 to 4.0 to 1 have been effective for administering and maintaining increased levels of biologically active macromolecules in vivo..

Especially preferred compositions of the invention are with bovine growth hormone, and water, aqueous buffer solution, or saline include dextrin; dextran; a heteropolysaccharide of glucose, galactose, mannose, glucuronic acid and fucose (Biopolymer PS-87 Lever Brothers Company), as described in U.S. Pat. No. 4,357,423; and mixtures of xanthan gum with locust bean gum.

The invention is further illustrated by the following nonlimiting examples.

EXAMPLE 1

Preparation of an Aqueous Bovine Growth Hormone Composition

A low viscosity corn dextrin (18 g), having the properties of being acidic as a 25% dispersion with a viscosity of 50 centipoise at 250° C., and bovine growth hormone (0.18 g) is admixed with 15 ml of carbonate buffer saline, pH 9.4 ($Na_2CO_3$, 0.025 mol; $NaHCO_3$ 0.025 mol; and NaCl 0.15 mol) until a homogenous paste is obtained.

EXAMPLE 2

Evaluation of Growth Hormone Compositions of the Invention in Dairy Cows

Nine lactating cows are divided into three groups of three. Throughout the test, all cows are fed the same ration of corn silage, alfalfa hay, and dairy concentrate adequate to produce 25 kg to 30 kg of milk per day. The cows are not treated for one week and daily milk production and bovine growth hormone blood levels obtained for each group of three animals. The experimental treatments listed in Table I below are administered during weeks two, three and four and the bovine growth hormone blood levels determined at two, four and six hours after injection and daily thereafter by established radioimmunoassay procedures.

TABLE I

| Treatment Administered |
| --- |
| A. Control - 3 cows |
| B. bGH in dextrin solution. 175 mg bGH once/week - 3 cows |
| C. bGH in buffered saline, 25 mg bGH/day - 3 cows |

All injections are administered subcutaneously.

The results of these experiments which are summarized in Table II below demonstrate the effectiveness of the compositions of the invention in providing sustained release of bovine growth hormone. Comparable results are obtained with other compositions of the invention.

Table III below which summarizes the milk production of these animals and demonstrates the effectiveness of the compositions of the invention for increasing the milk production of animals treated with these compositions.

TABLE II

| Average[1] Bovine Growth Hormone Blood Levels in ng/ml (nanograms/ml) | | | |
| --- | --- | --- | --- |
| Time After Treatment | A (Control) | B (Injected Day 0, 7, 14) | C (Injected Daily) |
| 2 hr | 2.9 | 7.1 | 23.0 |
| 4 hr | 3.3 | 9.9 | 9.9 |
| 6 hr | 2.8 | 21.6 | 5.7 |
| 1 day | 3.2 | 65.4 | 4.4 |
| 2 day | 2.9 | 36.4 | 4.5 |
| 3 day | 2.8 | 16.3 | 4.6 |
| 4 day | 2.5 | 16.5 | 4.6 |
| 5 day | 3.2 | 26.1 | 7.6 |
| 6 day | 2.7 | 12.9 | 3.1 |
| 7 day | 4.5 | 17.6 | 5.3 |
| 14 day | 3.9 | 22.9 | 8.7 |

TABLE II-continued

Average[1] Bovine Growth Hormone Blood Levels in ng/ml (nanograms/ml)

| Time After Treatment | A (Control) | B (Injected Day 0, 7, 14) | C (Injected Daily) |
|---|---|---|---|
| 18 day | 8.1 | 31.6 | 10.7 |

[1] Average of 3 animals rounded to the nearest 0.1

TABLE III

Weekly Average[1] Milk Production

| Treatment | B Milk Kg | % Increase[2] | C Milk Kg | % Increase[2] |
|---|---|---|---|---|
| 7 day pretreatment | 22.33 | — | 23.39 | — |
| Week one of treatment | 24.77 | 10.9 | 27.81 | 16.8 |
| Week two of treatment | 26.81 | 20.1 | 29.97 | 28.1 |
| Week three of treatment | 26.26 | 17.6 | 28.32 | 21.0 |

[1] Average of three (3) cows
[2] Normalized increase over pretreatment levels

EXAMPLE 3

Sustained Release of Compositions of the Invention in Sheep

Utilizing essentially the same procedure as Example 1 the compositions listed in Table VI below are administered to two groups of sheep (three animals per group). Daily blood samples are obtained for a 5 day period and assayed for bGH blood levels as previously described. The results of these experiments which are summarized in Table V below; demonstrate the effectiveness of the compositions of the invention for maintaining elevated levels of growth hormone in the blood for extended periods of time.

TABLE IV

| Composition | D | E |
|---|---|---|
| bgH | 30 mg | 30 mg |
| Dextrin | 3 g | 1.5 g |
| Carboxymethyl-cellulose | None | 0.163 g |
| Carbonate Buffered Saline | To 5 ml | To 5 ml |

Compositions Administered

TABLE V

Average[1] Bovine Growth Hormone Blood Levels ng/ml of Sheep

| Composition | D | E |
|---|---|---|
| 0 hr | 4.1 | 2.6 |
| 2 hr | 35.0 | 19.0 |
| 4 hr | 39.0 | 23.0 |
| 6 hr | 71.0 | 23.0 |
| 1 day | 161.5 | 149.1 |
| 2 day | 17.7 | 22.2 |
| 3 day | 12.0 | 13.8 |
| 4 day | 51.9 | 9.8 |
| 5 day | 113.1 | 31.4 |

[1] Average of three (3) animals

EXAMPLE 4

Sustained Release of Compositions of the Invention in Sheep

Utilizing essentially the same procedure as Example 2 the compositions listed in Table VI below are administered to two groups of sheep (three animals per group). Daily blood samples are obtained for a 5 day period and periodically thereafter and assayed for bGH blood levels as previously described. The results of these experiments which are summarized in Table VII below, demonstrate the effectiveness of the compositions of the invention for maintaining elevated levels of growth hormone in the blood for extended periods of time.

TABLE VI

Compositions Administered

| Composition | F | G | H |
|---|---|---|---|
| bGH | 56 mg | 63 mg | 23.8 mg |
| heteropolysaccharide (Biopolymer PS-87 Lever Brothers Co) | 100 mg | 100 mg | 100 mg |
| Water | 5 ml | — | — |
| Carbonate Buffered Saline (CBS) | — | 5 ml | — |
| 70% Sorbitol/CBS | — | — | To 5 g |

TABLE VII

Average[1] Bovine Growth Hormone Blood Levels ng/ml of Sheep

| Composition Day | F | G | H |
|---|---|---|---|
| 0 | 2.4 | 1.3 | 4.5 |
| 1 | 152.4 | 103.4 | 140.9 |
| 2 | 38.2 | 32.9 | 53.8 |
| 3 | 20.0 | 23.1 | 36.7 |
| 4 | 18.1 | 17.3 | 30.7 |
| 5 | 17.1 | 14.7 | 25.1 |
| 6 | 10.0 | 12.3 | 28.4 |
| 8 | 18.3 | 22.9 | 29.6 |
| 10 | 97.2 | 18.8 | 26.0 |
| 13 | 14.7 | 16.2 | 11.9 |
| 15 | 9.8 | 11.6 | 9.6 |
| 17 | 7.7 | 11.0 | 8.3 |
| 20 | 9.1 | 9.2 | 5.8 |

[1] Average of three (3) animals

EXAMPLE 5

Sustained Release of Compositions of the Invention in Sheep

Utilizing essentially the same procedure as Example 2 the compositions listed in Table VIII below are administered to two groups of sheep (three animals per group). Daily blood samples are obtained for a 5 day period and periodically thereafter assayed for bGH blood levels as previously described. The results of these experiments which are summarized in Table IX below, demonstrate the effectiveness of the compositions of the invention for maintaining elevated levels of growth hormone in the blood for extended periods of time.

TABLE VIII

Compositions Administered

| Composition | I | J |
|---|---|---|
| bGH | 64.4 mg | 35 mg |
| Guar gum | 250 mg | — |
| Carrageenan | — | 125 mg |
| Saturated Boric acid solution pH 9.4 | To 5 ml | — |
| Water | — | To 5 ml |

TABLE IX

Average[1] Bovine Growth Hormone Blood Levels ng/ml of Sheep

| Composition Day | I | J |
|---|---|---|
| 0 | 4.4 | 4.5 |
| 1 | 5.9 | 75.0 |

TABLE IX-continued

Average[1] Bovine Growth Hormone Blood Levels ng/ml of Sheep

| Composition Day | I | J |
|---|---|---|
| 2 | 6.4 | 32.2 |
| 3 | 6.1 | 19.7 |
| 4 | 4.9 | 14.9 |
| 5 | 6.8 | 8.5 |
| 6 | 15.4 | 11.1 |
| 8 | 46.6 | 8.6 |
| 10 | 58.3 | 16.7 |
| 13 | 29.7 | 12.7 |
| 15 | 38.4 | — |
| 17 | 23.7 | 20.0 |

[1] Average of three (3) animals

EXAMPLE 6

Sustained Release of Compositions of the Invention in Sheep

Utilizing essentially the same procedure as Example 2 the compositions listed in Table X below are administered to two groups of sheep (three animals per group). Daily blood samples are obtained for a 5 day period and assayed for bGH blood levels as previously described. The results of these experiments which are summarized in Table XI below, demonstrate the effectiveness of the compositions of the invention for maintaining elevated levels of growth hormone in the blood for extended periods of time.

TABLE XI-continued

Average[1] Bovine Growth Hormone Blood Levels ng/ml of Sheep

| Composition Day | K | L | M | N | O | P |
|---|---|---|---|---|---|---|
| 13 | 7.7 | 6.0 | 6.7 | 3.9 | 7.5 | 34.2 |
| 15 | 9.1 | 5.2 | 6.0 | 4.4 | 7.3 | 31.8 |
| 17 | 11.8 | 4.4 | 2.9 | 4.7 | 6.2 | 51.6 |

EXAMPLE 7

Evaluation of Growth Hormone Compositions of the Invention in Dairy Cows

Lactating cows are divided into groups of four or five. Throughout the test, fill cows are fed the same ration of corn silage, alfalfa hay, and dairy concentrate adequate to produce 25 kg to 30 kg of milk per day. The cows are not treated for two weeks and daily milk production levels obtained for each group of animals. The experimental treatments listed in Table XII below are administered during week three, and milk production data for the treated animals and a group of untreated (control) animals recorded daily.

TABLE XII

| Composition | Treatment Administered | | | | |
|---|---|---|---|---|---|
|  | 1 | 2 | 3 | 4 | 5 |
| bGH | 350 mg | 350 mg | 350 mg | 350 mg | 350 mg |
| Xanthan gum | — | — | — | 300 mg | 300 mg |
| Locust bean gum | — | — | — | 200 mg | 200 mg |
| Heteropoly saccaharide (Biopolymer PS-87 Lever Brothers Co) | 500 mg | 400 mg | 200 mg | — | — |
| Water | To 25 g | To 20 g | To 10 g | — | — |
| 70% Sorbitol/saline | — | — | — | To 10 g | — |
| Propylene glycol/saline | — | — | — | — | To 10 g |

The results of these experiments which are summarized in Table XIII below summarizes the milk productions of these animals and demonstrates the effectiveness of the compositions of the invention for increasing the milk production for extended periods of time of animals treated with these compositions.

TABLE X

| Composition | Compositions Administered | | | | | |
|---|---|---|---|---|---|---|
|  | K | L | M | N | O | P |
| bSTH | 51.8 mg | 51.8 mg | 51.8 mg | 51.8 mg | 23.8 mg | 64.4 mg |
| Xanthan gum | 150 gm | 150 gm | 150 gm | 150 gm | 125 gm | None |
| Locust Bean gum | 100 gm | 100 gm | 100 gm | 100 gm | None | 250 gm |
| Water | To 5 g | None | None | 2350 mg | None | To 5 ml |
| 70% Sorbitol/water | None | To 5 g | None | None | None | None |
| Propylene glycol | None | None | To 5 g | 2350 mg[2] | None | None |
| CBS/70% Sorbitol | None | None | None | None | To 5 g | None |

[2] bGH dispersed/dissolved in water, gums dispersed in propylene glycol, and the aqueous solution is added to suspension.

TABLE XI

Average[1] Bovine Growth Hormone Blood Levels ng/ml of Sheep

| Composition Day | K | L | M | N | O | P |
|---|---|---|---|---|---|---|
| 0 | 2.4 | 4.1 | 1.2 | 1.9 | 2.9 | 2.7 |
| 1 | 148.9 | 160.7 | 14.00 | 108.7 | 107.9 | 125.1 |
| 2 | 60.6 | 45.5 | 5.3 | 25.6 | 39.3 | 44.5 |
| 3 | 49.6 | 29.8 | 5.4 | 18.0 | 24.2 | 19.2 |
| 4 | 35.6 | 28.0 | 5.8 | 14.1 | 26.8 | 15.5 |
| 5 | 29.2 | 23.4 | 7.8 | 11.8 | 18.7 | 28.0 |
| 6 | 24.8 | 20.2 | 10.8 | 8.5 | 19.1 | 40.9 |
| 8 | 17.2 | 14.8 | 15.8 | 9.5 | 19.2 | 48.3 |
| 10 | 8.7 | 9.9 | 12.5 | 5.5 | 14.5 | 47.9 |

TABLE XIII

Daily Average Percentage Increase in Milk Production over an Untreated Control

| Treatment Day | 1[3] | 2[3] | 3[3] | 4[4] | 5[4] |
|---|---|---|---|---|---|
| 0 | 0.75 | −.49 | 5.30 | 1.85 | 1.41 |
| 1 | 10.52 | 7.35 | 6.97 | 8.95 | 9.14 |
| 2 | 12.10 | 8.84 | 13.14 | 10.40 | 11.22 |
| 3 | 10.60 | 8.05 | 11.96 | 7.79 | 14.85 |
| 4 | 9.74 | 13.02 | 12.29 | 5.15 | 11.49 |
| 5 | 10.81 | 13.10 | 9.79 | 1.80 | 3.79 |
| 6 | 3.47 | 4.48 | 6.92 | 6.26 | 1.27 |
| 7 | 5.16 | 3.18 | 3.46 | 5.29 | 6.99 |
| 8 | 1.24 | 1.17 | 4.50 | 8.37 | 9.49 |
| 9 | .03 | 0.55 | −1.57 | 7.37 | 9.78 |

TABLE XIII-continued

Daily Average Percentage Increase in Milk Production over an Untreated Control

| Treatment Day | 1[3] | 2[3] | 3[3] | 4[4] | 5[4] |
| --- | --- | --- | --- | --- | --- |
| 10 | −3.26 | −2.02 | −2.14 | 5.78 | 6.11 |
| 11 | 1.51 | −0.56 | −.54 | 6.25 | 2.44 |
| 12 | −.80 | −3.44 | −3.89 | 3.35 | 3.50 |
| 13 | −1.12 | −2.45 | −5.42 | 5.17 | −.32 |
| 14 | −1.27 | −0.22 | −5.17 | 4.08 | −1.04 |

[3]Average of four cows
[4]Average of five cows

EXAMPLE 8

1.2 g of the dextrin PZ/9 (Reppe, Vaxjo) is dissolved in 1 ml water by heating. To the room temperatured solution, 100 μl bovine growth hormone (150 mg/ml) is added. After careful mixing the bovine growth hormone is determined with the help of an ELISA method. The result shows that only about 5% of the hormone added could be detected. When the detergent Triton X100 is added, in increments, the more detergent, added, the more hormone could be detected. At a detergent concentration of 4% all the added hormone could be detected, which indicates strong complex formation between the protein and the carbohydrate. The detergent Triton X-100 is used in biochemical work where dissociation of strong hydrophobic interactions is needed. If detergents which do not have this capability (e.g. TWEEN 80 ) is added a corresponding dissociation of the complex is not seen.

EXAMPLE 9

A mixture prepared by the procedure of Example 8 kept in physiological buffer (PBS) for five days without adding any type of detergent, only 1% of the hormone added can be detected on day five. If now a 4% Triton solution is added one may, as was seen in Example 8 detect 100% of the hormone added.

EXAMPLE 10

If the mixture according to Example 8 is kept for four days but with various and successively higher concentrations of Triton X100, the result is that with a concentration of 0.05%, about 5% of the hormone is dissociated and is detected with the ELISA determination. At a concentration of 0.08%, about 15% of the hormone has been released after five days , at the concentration of 0. 25%, about 20% of the hormone is dissociated and at a concentration of 1% about 30% of the hormone has been dissociated from the complex.

EXAMPLE 11

If the dextran T500 (Pharmacia AB, Uppsala) with a concentration of 0.35 g/ml is used as the carbohydrate, a similar dissociation as described in Example 9 is seen.

EXAMPLE 12

If radioactively labelled hormone, is incorporated as described in Example 8 or 11 and the amount of radioactive material is determined after filtration through a 50 nanometer filter, the result is that 50% of the radioactivity passes through the filter. This indicates that despite half of the hormone passing the filter, only 10% of this fraction can be detected by the ELISA method, which means that 90% of the hormone in this fraction is hidden and can not be reached by the antibodies in the ELISA. The result indicates that the hormone is masqued or hidden for detection, since association between the protein and the antibody can not be obtained.

EXAMPLE 13

If the mixture according to Example 8 is injected as a single injection to a hypox rat, which has no production of growth hormone, a continuous growth over seven days is seen. In this case the total amount of hormone injected is 2 mg. If the same amount is injected without complex formation with a carbohydrate, the rat shows a rapid growth during the first 24 hours but after this the rat loses weight.

What is claimed is:

1. A biologically active slow release composition which comprises a homogenous mixture of a water soluble carbohydrate polymer or a water dispersible carbohydrate polymer, a growth promoting effective amount or a milk production enhancing effective amount of a biologically active macromolecule and an aqueous or a pharmaceutically acceptable water miscible organic solvent; wherein said macromolecule is a growth hormone, a somatomedin or a biologically active fragment thereof; with the proviso that the weight ratio of the carbohydrate polymer to said macromolecule is in the range of 0.25:1.0 to 100:1.0 and the weight ration of the aqueous or pharmaceutically acceptable water miscible solvent to carbohydrate polymer is in the range of 0.83:1.0 to 50:1.0.

2. The composition according to claim 1, wherein the biologically active macromolecule is bound to the carbohydrate polymer forming a complex.

3. The composition according to claim 2, wherein the mixture further contains a hydrophobic dissociating substance or a hydrophilic dissociating substance.

4. The composition according to claim 1, wherein the solvent is an aqueous buffered solution or saline.

5. The composition according to claim 2, 3 or 4, wherein the carbohydrate is starch or dextran.

6. The composition according to claim 4, wherein the carbohydrate polymer is dextran, dextrin, alginate, starch, fractionated starch, glycogen, pullullan, agarose, cellulose, chitosan, carrageenan, synthetic biopolymer, xanthan gum, guar gum, locust bean gum, gum arabic, tragacanth gum, karaya gum or a mixture thereof; and the growth hormone is bovine growth hormone, ovine growth hormone, equine growth hormone or porcine growth hormone.

7. The composition according to claim 6, wherein the carbohydrate polymer is dextrin; the growth hormone is bovine growth hormone and the solvent is water or an aqueous buffered solution.

8. The composition according to claim 6, wherein the carbohydrate polymer is a heteropolysaccharide of glucose, galactose, mannose, glucuronic acid and fucose and the growth hormone is bovine growth hormone.

9. The composition according to claim 6, wherein the mixture of carbohydrate polymers is a mixture of xanthan gum and locust bean gum and hormone.

10. A biologically active slow release composition which comprises an aqueous solution, a complex of a growth promoting effective amount or a milk production enhancing effective amount of a biologically active macromolecule selected from the group consisting of a growth hormone, a somatomedin and a biologically active fragment thereof bound to a water soluble or water dispersible carbohydrate polymer; with the proviso that the weight ratio of the carbohydrate polymer to said macromolecule is in the range of 0.25:1.0 to 100:1.0 and the weight ratio of the water of the aqueous solution to carbohydrate polymer is in the range of 0.83:1.0 to 50:1.0.

11. A method of preparing a biologically active slow release composition comprising mixing a growth promoting effective amount or a milk production enhancing effective amount of a biologically active macromolecule selected from the group consisting of a growth hormone, a somatomedin and a biologically active fragment thereof with a water soluble or water dispersible carbohydrate polymer in an aqueous solvent without forming a covalent bond between said biologically active macromolecule and said carbohydrate polymer, wherein the weight ratio of the carbohydrate polymer to said macromolecule is in the range of 0.25:1.0 to 100:1.0 and the weight ratio of the aqueous solvent to carbohydrate polymer is in the range of 0.83:1.0 to 50:1.0, thereby obtaining a homogenous mixture.

12. The method according to claim 11, further comprising the step of adding a hydrophobic dissociating substance or a hydrophilic dissociating substance in the mixing step when said mixing step creates a noncovalent bond between the biologically active macromolecule and the carbohydrate polymer.

* * * * *

UNITED STATES PATENT AND TRADEMARK OFFICE
CERTIFICATE OF CORRECTION

PATENT NO. : 5,266,333
DATED : Nov. 30, 1993
INVENTOR(S) : Susan M. Cady, et al.

It is certified that error appears in the above-indentified patent and that said Letters Patent is hereby corrected as shown below:

<u>Claim 1, line 21, col. 10</u>

"ble organie solvent; wherein said macromolecule is a" should read

--"ble organic solvent; wherein said macromolecule is a"--

<u>Claim 1, line 26, col. 10</u>

"ration of the aqueous or pharmaceutically acceptable" should read

--"ratio of the aqueous or pharmaceutically acceptable"--

UNITED STATES PATENT AND TRADEMARK OFFICE
CERTIFICATE OF CORRECTION

PATENT NO. : 5,266,333
DATED : Nov. 30, 1993
INVENTOR(S) : Susan M. Cady, et al, It is certified that error appears in the above-indentified patent and that said Letters Patent is hereby corrected as shown below:

<u>Claim 9, line 59, col. 10</u>

"than gum and locust bean gum and hormone."

should read

--"than gum and locust bean gum and the growth hormone is bovine growth hormone."--

Signed and Sealed this

Twenty-sixth Day of July, 1994

Attest:

BRUCE LEHMAN

Attesting Officer

Commissioner of Patents and Trademarks